(12) United States Patent
Wang

(10) Patent No.: US 9,541,833 B2
(45) Date of Patent: Jan. 10, 2017

(54) POLYETHER COMPOUND, METHOD FOR PREPARING SAME AND PHOTORESIST COMPOSITION

(71) Applicant: BOE TECHNOLOGY GROUP CO., LTD., Beijing (CN)

(72) Inventor: Xuelan Wang, Beijing (CN)

(73) Assignee: BOE Technology Group Co., Ltd., Beijing (CN)

( * ) Notice: Subject to any disclaimer, the term of this patent is extended or adjusted under 35 U.S.C. 154(b) by 232 days.

(21) Appl. No.: 14/366,382

(22) PCT Filed: Nov. 25, 2013

(86) PCT No.: PCT/CN2013/087790
§ 371 (c)(1),
(2) Date: Jun. 18, 2014

(87) PCT Pub. No.: WO2015/024316
PCT Pub. Date: Feb. 26, 2015

(65) Prior Publication Data
US 2016/0154305 A1    Jun. 2, 2016

(30) Foreign Application Priority Data

Aug. 20, 2013 (CN) .......................... 2013 1 0363403

(51) Int. Cl.
| G03F 7/032 | (2006.01) |
| G03F 7/027 | (2006.01) |
| G03F 7/11 | (2006.01) |
| G03F 7/004 | (2006.01) |
| C08G 65/332 | (2006.01) |
| C07C 15/50 | (2006.01) |
| C07C 15/54 | (2006.01) |
| C08G 65/48 | (2006.01) |
| G03F 7/09 | (2006.01) |
| G03F 7/00 | (2006.01) |
| G02B 5/20 | (2006.01) |
| H01L 21/027 | (2006.01) |

(52) U.S. Cl.
CPC .............. G03F 7/11 (2013.01); C07C 15/50 (2013.01); C07C 15/54 (2013.01); C08G 65/332 (2013.01); C08G 65/48 (2013.01); G03F 7/004 (2013.01); G03F 7/027 (2013.01); G03F 7/094 (2013.01); G02B 5/20 (2013.01); G03F 7/0007 (2013.01); H01L 21/0271 (2013.01)

(58) Field of Classification Search
CPC ................................ G03F 7/027; G03F 7/007
See application file for complete search history.

(56) References Cited

U.S. PATENT DOCUMENTS

| 4,460,715 A | 7/1984 | Hoffman et al. |
| 5,738,971 A * | 4/1998 | Suzuki ..................... G03F 7/027 430/288.1 |
| 5,935,761 A | 8/1999 | Hwang et al. |
| 5,981,147 A | 11/1999 | Hallock et al. |
| 6,355,702 B1 * | 3/2002 | Ober ................. C08F 222/1006 560/97 |
| 8,318,053 B2 | 11/2012 | Choi et al. |
| 9,006,352 B2 | 4/2015 | Li et al. |
| 9,365,505 B2 * | 6/2016 | Wang ..................... C07C 303/26 |
| 2006/0212011 A1 * | 9/2006 | Popp ....................... C07C 67/08 604/372 |
| 2007/0139501 A1 * | 6/2007 | Sekiguchi .............. C09D 11/38 347/100 |
| 2008/0004686 A1 * | 1/2008 | Hunt ..................... A61F 2/2418 623/1.11 |
| 2008/0081270 A1 * | 4/2008 | Tanaka ................... C08F 22/00 430/7 |
| 2011/0070481 A1 | 3/2011 | Liang et al. |
| 2011/0189291 A1 * | 8/2011 | Yang ................. A61K 31/5377 424/486 |

(Continued)

FOREIGN PATENT DOCUMENTS

| CN | 1205784 A | 1/1994 |
| CN | 1143418 A | 2/1997 |

(Continued)

OTHER PUBLICATIONS

English translation of CN 103351465 a obtained from EPO website on Jul. 11, 2016 35 pages.*
International Search Report, International Preliminary Report on Patentability and Written Opinion of the International Searching Authority of PCT/CN2013/087790 in Chinese, mailed May 21, 2014.
Chinese Office Action of Chinese Application No. 201310363403.8, mailed Mar. 25, 2015 with English translation.

(Continued)

Primary Examiner — Cynthia Hamilton
(74) Attorney, Agent, or Firm — Collard & Roe, P.C.

(57) ABSTRACT

A polyether compound which is as shown in Formula (I), wherein $R_1$ is a polyether backbone of the polyether polyol; $R_2$ is hydrogen or $C_1$–$C_5$ alkyl; n is 3, 4 or 5. Furthermore, a photoresist composition comprising the polyether compound is disclosed. This photoresist composition is used to make the colored layer in a colored film substrate, in which the polymer film layer thus obtained has a small edge slope angle and is not prone to light leakage.

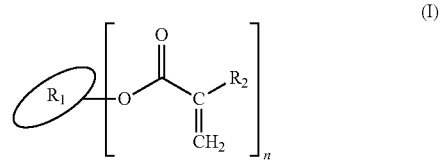

(I)

8 Claims, 4 Drawing Sheets

(56) References Cited

U.S. PATENT DOCUMENTS

2012/0161087 A1    6/2012  Jung et al.
2012/0161088 A1*   6/2012  Choi ..................... G03F 7/0388
                                                            430/286.1

FOREIGN PATENT DOCUMENTS

| CN | 1303876 | A |   | 7/2001 |
|----|---------|---|---|--------|
| CN | 1529206 | A |   | 9/2004 |
| CN | 101633805 | A | | 1/2010 |
| CN | 102540716 | A | | 7/2012 |
| CN | 102558459 | A | | 7/2012 |
| CN | 102566265 | A | | 7/2012 |
| CN | 102786631 | A | | 11/2012 |
| CN | 102830589 | A | | 12/2012 |
| CN | 103351465 | a | * | 10/2013 |
| DE | 10 2011 106 039 | A1 | | 1/2013 |
| TW | 201227174 | A | | 7/2012 |
| TW | 201229664 | A | | 7/2012 |

OTHER PUBLICATIONS

English Translation of the International Search Report of PCT/CN2013/087790 published in English on Feb. 26, 2015.
English translation of the International Preliminary Report on Patentability and Written Opinion of the International Searching Authority of PCT/CN2013/087790, issued Feb. 23, 2016.

\* cited by examiner

POLYETHER COMPOUND, METHOD FOR PREPARING SAME AND PHOTORESIST COMPOSITION

This application is the National Stage of PCT/CN2013/087790 filed on Nov. 25, 2013, which claims priority under 35 U.S.C. §119 of Chinese Application No. 201310363403.8 filed on Aug. 20, 2013.

TECHNICAL FIELD

Embodiments of the invention relate to a polyether compound for photoresist, a method for preparing the same, as well as a photoresist composition comprising the polyether compound.

BACKGROUND

The quality of the colored substrate, an important component of a liquid crystal display, directly affects the quality of the liquid crystal display. A colored substrate generally comprises a colored layer formed from three colored photoresists (red, green, and blue). In a colored substrate, there are some requirements on the slope angle of the edge of the colored film layer. If the slope angle is too large, it may cause the missing of an orientation layer during the subsequent orientation layer coating process, thereby making it prone to light leakage.

Currently, the colored layer is often formed by exposure and development on a colored photoresist. A colored photoresist primarily comprises a polymerizable monomer, an alkaline soluble resin, a pigment dispersion, a photoinitiator, a solvent, and the like. After exposure and high temperature post-baking, the polymerizable monomer will polymerize to form a polymer. However, based on empirical data obtained by comparing the high temperature post-baking of various monomers, polymers formed from common polymerizable monomers have too high hardness which causes high brittleness of the edge of the film layer and poor fluidity under gravity, making it not prone to bending and depressing, which results in a smooth slope with a high slope angle, usually higher than 75°, making it prone to light leakage.

SUMMARY

Embodiments of the invention provide polyether compound for photoresist which can significantly ameliorate the issue of too large slope angle at the edge of a film layer.

Embodiments of the invention further provide a method for preparing the polyether compound as well as a photoresist composition.

In one aspect, the invention provides a polyether compound which is as shown in Formula (I):

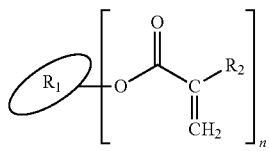

(I)

wherein $R_1$ is a polyether backbone of the polyether polyol; $R_2$ is hydrogen or $C_1$~$C_5$ alkyl; n is 3, 4 or 5.

For example, the number of the polymerizable monomers in $R_1$ may be an integer larger than and equal to 20, and less than and equal to 100.

In another aspect, the invention provides a method for preparing the polyether compound, comprising undergoing esterification between the polyether polyol as shown in Formula (I-1) and the acryloyl chloride compound as shown in Formula (I-2) in the presence of a catalyst in an organic solvent; wherein the catalyst is triethylamine; and the organic solvent is tetrahydrofuran;

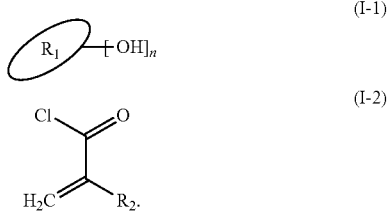

In a further aspect, the invention provides a photoresist composition comprising a polymerizable monomer which comprises the polyether compound of any one of the aforesaid technical solutions, wherein the polymerizable monomer comprises 10%~25% by weight of polyether compound.

For example, the photoresist composition comprises by weight the following raw materials:
polymerizable monomer: 15~25 fractions;
alkaline soluble resin: 5~25 fractions;
pigment dispersion: 30~50 fractions;
photoinitiator 1~10 fractions; and
solvent: 15~40 fractions.

For example, the photoresist composition may further comprise 0.0095~0.445 fraction of adjuvant.

For example, the adjuvant may be one or more of leveling agents, anti-foams, surfactants, slipping agents, silane coupling agents or light stablizers.

For example, the polymerizable monomer may further comprise one or more of dipentaerythritol pentaacrylate, trihydroxymethylpropane triacrylate, pentaerythritol tetraacrylate or aromatic urethane acrylate.

For example, the alkaline soluble resin may be an alkaline soluble acrylate resin.

For example, the photoinitiator may be one or more of acyl phosphosphine oxide, ketone oxime ester, benzophenone, benzoin, anthraquinone, aryl ketone or iron arene photoinitiators.

For example, the solvent may be one or more of propylene glycol monomethyl ether acetate, propylene glycol diacetate, ethyl 3-ethoxy-3-iminopropionate, 2-heptane, 3-heptane, cyclopentanone or cyclohexanone.

The polyether chain containing polyether compound provided in the invention can be used as the polymerizable monomer in a photoresist. The photoresist composition provided in the invention can be used to make the colored layer in a colored film substrate; the polymer film layer obtained after the polymerization of the polymerizable monomer has a small edge slope angle and is not prone to light leakage, thereby enabling good quality of the display device thus manufactured.

DESCRIPTION OF DRAWINGS

In order to more clearly illustrate the technical solutions of the invention, the figures of the invention are briefly introduced below. Apparently, the figures in the following description merely involve a few embodiments of the invention, rather than limit the invention.

DETAILED DESCRIPTION

Figure 1:
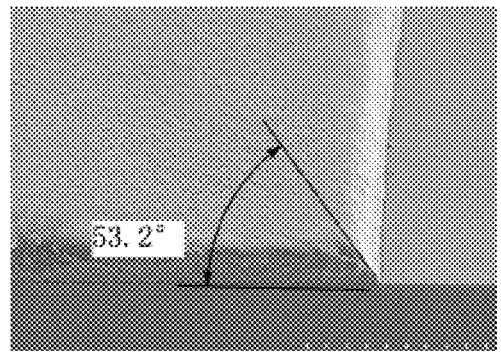
FIG. 1 is a scanning electron microscopy image of the cross section of the edge of the film layer after the photoresist composition obtained in Example 1 is made into the film.

In order to make the purpose, technical solutions and advantages of the embodiments of the invention clearer, the technical solutions of the embodiments of the invention will be clearly and completely described in relation to the drawings of the embodiments of the invention. Apparently, the described embodiments are merely some, rather than all embodiments of the present invention. All other embodiments obtainable by a person of ordinary skill in the art based on the embodiments described in the invention without inventive work fall into the scope of the invention.

Embodiments of the invention provides a polyether compound which is a polyether compound as shown in Formula (I):

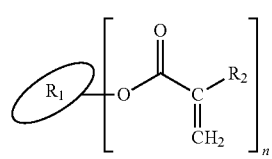

(I)

wherein $R_1$ is a polyether backbone of the polyether polyol; $R_2$ is hydrogen or $C_1\sim C_5$ alkyl; n is 3, 4 or 5.

In a preferred embodiment, the number of the polymerizable monomers in $R_1$ is an integer larger than and equal to 20, and less than and equal to 100.

A method for preparing the polyether compound provided in an embodiment of the invention may be as follows: undergoing esterification between the polyether polyol as shown in Formula (I-1) and the acryloyl chloride compound as shown in Formula (I-2) in the presence of a catalyst in an organic solvent; wherein the catalyst is triethylamine; and the organic solvent is tetrahydrofuran;

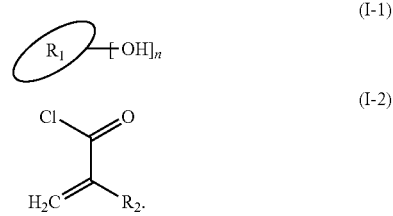

The aforesaid preparative method may be performed according to the present disclosure, or may be performed according to a conventional esterification reaction between an alcohol and an acyl chloride, for example, performed in an organic solvent in the presence of an alkali.

An embodiment of the invention provides a photoresist composition comprising a polymerizable monomer which comprises any one of the aforesaid polyether compounds, wherein the polymerizable monomer comprises 10%~25% by weight of polyether compound.

In a preferred embodiment, the photoresist composition comprises by weight the following raw materials (weight fractions):

polymerizable monomer: 15~25 fractions;

alkaline soluble resin: 5~25 fractions;

pigment dispersion: 30~50 fractions;

photoinitiator: 1~10 fractions; and solvent: 15~40 fractions.

The photoresist composition of the embodiment of the invention may comprise an adjuvant commonly used for the photoresist composition. The adjuvant includes but is not limited to a leveling agent, an anti-foam, a surfactant, a slipping agent, a silane coupling agent, a light stabilizer, and the like, and may include one or more of the aforesaid agents. The choice of the type as well as the amount used of the adjuvant may be determined by a person skilled in the art based on practical need. Preferably, the amount of the adjuvant is 0.0095~0.445 weight fraction.

In the photoresist composition of the embodiments of the invention, other than the aforesaid polyether compound, the polymerizable monomer may be selected from any one of the polymerizable monomer traditionally used for the photoresist composition, which includes but is not limited to one or more of dipentaerythritol pentaacrylate, trihydroxymethylpropane triacrylate, pentaerythritol tetraacrylate, and aromatic urethane acrylate, and the like. In some examples, the polymerizable monomer may be selected from the following monomers:

(1) Dipentaerythritol Pentaacrylate

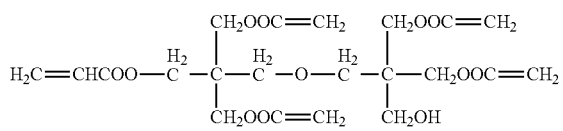

(2) Trihydroxymethylpropane Triacrylate

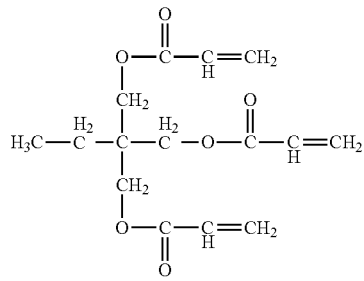

(3) Pentaerythritol Tetraacrylate

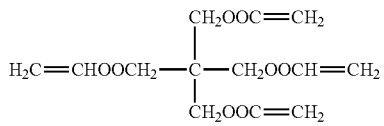

In the photoresist composition of the embodiments of the invention, the pigment dispersion maybe any one of the pigment dispersion traditionally used for the photoresist composition. The embodiments of the invention do not specifically limit the color of the encompassed pigment. A suitable color may be chosen according to the colored layer actually to be formed, which includes but is not limited to a red pigment, a green pigment, a yellow pigment, a blue pigment, a violet pigment, a cyano pigment, a black pigment and the like, and may be one or more. The embodiments of the invention does not specifically limit the components of the pigment and any existing organic pigment can be used, for example, including but not limited to the following: one or more of monoazo yellow and orange pigments, diazo pigments, naphthol pigments, naphthol AS pigments, laked azo pigments, benzimidazolone pigments, diazo condensation pigments, phthalocyanine pigments, quinacridone pigments, thioindigo pigments, anthraquinone pigments, dioxazine pigments, triarylmethane pigments, diketopyrrolopyrrole pigments (DDP pigments), quinophthalone pigments and the like.

The pigment dispersion may comprise a pigment, a dispersing agent, a dispersing resin, an organic solvent, etc. It may be a commercial available product or prepared using an existent method, such as the methods disclosed in Chinese patent documents CN101659813B (for example, see paragraphs [0027]-[0143] of the description and Claims 1-13), CN101928489B (for example, see paragraphs [0013]-[0026] of the description and Claims 1-8), CN102977359A (for example, see paragraphs [0077]-[0112] of the description and Claims 1-16), CN103146262A (for example, see paragraphs [0042]-[0059] of the description and Claims 1-13), and the like.

In the photoresist composition of the embodiments of the invention, the alkaline soluble resin may be selected from any one of the alkaline soluble resins used for conventional photoresist compositions. Preferably, the alkaline soluble resin may be an alkaline soluble acrylate resin, wherein the acrylate resin may be an unmodified acrylate resin, or may be a modified acrylate resin, such as an amine modified acrylate resin, an aromatic acid methacrylate resin, urethane acrylate resin, and the like.

In the photoresist composition of the embodiments of the invention, the photoinitiator may be selected from any one of the photoinitiators used for conventional photoresist compositions. Preferably, the photoinitiator used may include, but is not limited to any one or more of acyl phosphosphine oxide, ketone oxime ester, benzophenone, benzoin, anthraquinone, aryl ketone, iron arene photoinitiator, and the like.

In the photoresist composition of the embodiments of the invention, the solvent may be selected from any one of the solvents used for conventional photoresist compositions, as long as it can dissolve or disperse other components in the photoresist composition and does not react with the aforesaid components and has certain volatility. The solvent used includes, but is limited to propylene glycol monomethyl ether acetate, propylene glycol diacetate, ethyl 3-ethoxy-3-iminopropionate, 2-heptane, 3-heptane, cyclopentanone, cyclohexanone, and the like. Preferably, the aforesaid solvent may be used along, or two or more solvents may be mixed for use.

The following examples are used to illustrate the invention, rather than limit the scope of the invention. Unless specifically indicated, all reagents used in the example are conventional, commercially available reagents, and the technical means used in the examples are conventional means well known to a person skilled in the art.

The unit "fraction" in the examples of the invention indicates relative ratio. For example, 1 fraction of polyether triol (molecular weight: 3190) and 3.6 fractions of acryloyl chloride by mole indicates the molar ratio between the polyether triol and the acryloyl chloride is 1:3.6. The "fraction" in a composition is a weight unit, that is, gram, kilogram, ton, jin, and shall be determined according to the actual circumstance.

Example 1

(1) Preparation of the Polyether Compound Monomer

In the aforesaid Formula (I), $R_1$ is the polyether backbone of the polyether triol; $R_2$ is hydrogen; and n is 3.

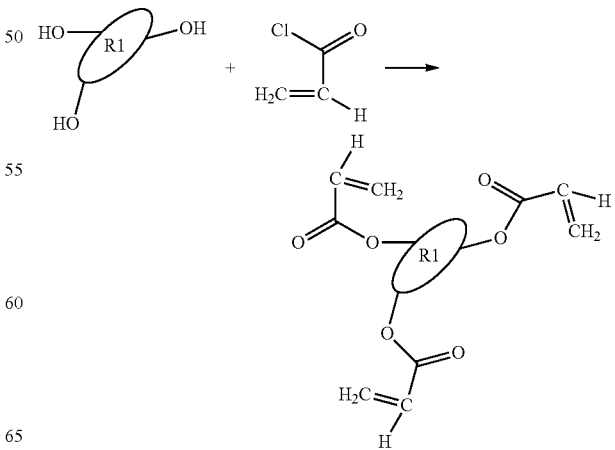

1 fraction of polyether triol (molecular weight: 3190), 0.10 fraction of the catalyst triethylamine, and 100 ml tetrahydrofuran solvent are added to the three-necked bottle by mole, and 3.6 fractions of acryloyl chloride are slowly added by dripping under ice bath. After completion of the dripping, the ice bath is removed, followed by heating to reflux under nitrogen atmosphere for 12 hours. After the completion of the reaction, 20 ml water is added under ice bath to quench the reaction, followed by filtration to remove salts and vacuum evaporation to remove tetrahydrofuran. 50 ml water is added, followed by extraction with ethyl acetate (3×100 ml). The organic layer (product) is dried with anhydrous sodium sulfate, and the solvent is spun dry under vacuum to provide the product.

The molecular weight of the product is detected by gel filtration spectrum to be 3352.

The gel filtration spectral testing method is as follows. TSP P100 high efficiency liquid chromatographer (manufactured by Thermoquest Ltd., USA) with GPC KF-803 chromatographic column. The mobile phase is tetrahydrofuran. The flow rate is 0.08 mL/min. The column temperature is kept at 30□. Detection is performed with RI150 refractive index detector. The concentration of the testing sample is 0.5% (w/v), using polystyrene as the molecular standard. Data analysis is performed using Jiangshen work station to provide the weight average molecular weight Mw. The gel filtration spectral testing method in the following examples is the same as this method.

(2) Preparation of the Photoresist Composition

The components are as follows (by weight fraction):
12 fractions of amine modified acrylate resin: the amino modified acrylate resin with the product name Laromer® LR 8997 is employed in the present example;
43 fractions of pigment dispersion: the pigment dispersion of the present example is obtained according to the disclosure of the Chinese Patent CN101659813B (Title: Pigment Dispersion, Pigment Photoresist, and Method for Preparing Same, published on Mar. 3, 2010);
18.3 fractions of dipentaerythritol pentaacrylate,
6.1 fractions of the aforesaid polyether compound;
3.5 fractions of the photoinitiator 2,4-dihydrobenzophenonone;
17.005 fractions of propylene glycol monomethyl ether acetate; and
0.01 fraction of the silane coupling agent KBM0-303, 0.04 fraction of the leveling agent BYK-380, 0.02 fraction of the anti-foam BYK-057, and 0.025 fraction of the light stablizer Chisorb 292.

The aforesaid components are mixed and thoroughly agitated to provide the photoresist composition 1.

Example 2

(1) Preparation of the Polyether Compound Monomer

In the aforesaid Formula (I), $R_1$ is the polyether backbone of the polyether tetrol; $R_2$ is methyl; and n is 4.

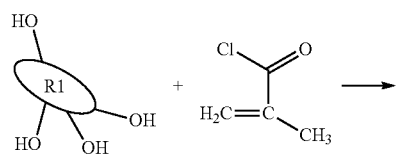

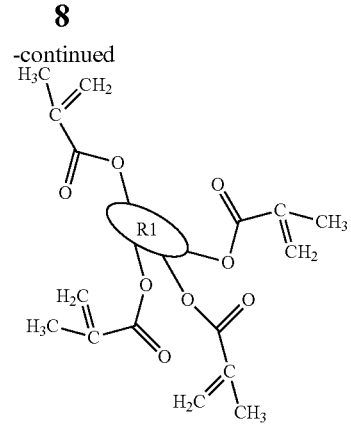

1 fraction of polyether tetrol (molecular weight: 4190), 0.15 fraction of the catalyst triethylamine, and 150 ml tetrahydrofuran solvent are added to the three-necked bottle by mole, and 4.6 fractions of 2-methacryloyl chloride are slowly added by dripping under ice bath. After completion of the dripping, the ice bath is removed, followed by heating to reflux under nitrogen atmosphere for 19 hours. After the completion of the reaction, 30 ml water is added under ice bath to quench the reaction, followed by filtration to remove salts and vacuum evaporation to remove tetrahydrofuran. 60 ml water is added, followed by extraction with ethyl acetate (3×120 ml). The organic layer (product) is dried with anhydrous sodium sulfate, and the solvent is spun dry under vacuum to provide the product.

The molecular weight of the product is detected by gel filtration spectrum to be 4432.

(2) Preparation of the Photoresist Composition

The components are as follows (by weight fraction):
8.59 fractions of aromatic acid methacrylate resin: the aromatic acid methacrylate resin with the product name Sarbox® SB400 is employed in the present example;
42.14 fractions of pigment dispersion: the pigment dispersion of the present example is obtained according to the disclosure of the Chinese Patent CN102977359A (application number: CN201210468331.9, title: Fluorine Containing Polymer, Method for Preparing Same, and Use thereof, Pigment Dispersion and Method for Preparing Same, published on Mar. 20, 2013);
20.889 fractions of trihydroxymethylpropane triacrylate,
2.321 fractions of the aforesaid polyether compound;
10 fractions of the photoinitiator benzoin butyl ether;
16.45 fractions of the propylene glycol diacetate and the cyclohexanone solvent (volume ratio: 9:1);
0.01 fraction of the silane coupling agent A-187, 0.23 fraction of the leveling agent BYK-354, 0.015 fraction of the anti-foam BYK-141, and 0.035 fraction of the light stablizer Chisorb 292.

The aforesaid components are mixed and thoroughly agitated to provide the photoresist composition 2.

Example 3

(1) Preparation of the Polyether Compound Monomer

In the aforesaid Formula (I), $R_1$ is the polyether backbone of the polyether pentol; $R_2$ is ethyl; and n is 5.

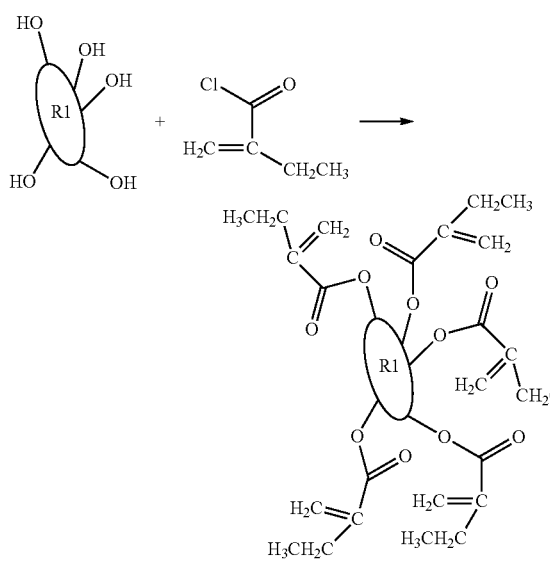

1 fraction of polyether pentol (molecular weight: 7280), 0.12 fraction of the catalyst triethylamine, and 200 ml tetrahydrofuran solvent are added to the three-necked bottle by mole, and 5.4 fractions of 2-ethylacryloyl chloride are slowly added by dripping under ice bath. After completion of the dripping, the ice bath is removed, followed by heating to reflux under nitrogen atmosphere for 25 hours. After the completion of the reaction, 35 ml water is added under ice bath to quench the reaction, followed by filtration to remove salts and vacuum evaporation to remove tetrahydrofuran. 80 ml water is added, followed by extraction with ethyl acetate (3×160 ml). The organic layer (product) is dried with anhydrous sodium sulfate, and the solvent is spun dry under vacuum to provide the product.

The molecular weight of the product is detected by gel filtration spectrum to be 7690.

(2) Preparation of the Photoresist Composition

The components are as follows (by weight fraction):

11.23 fractions of urethane acrylate resin: the urethane acrylate resin with the model name DH-317 of Shenzhen Dinghao Actinic Tech Co. Ltd. is employed in the present example.

33.38 fractions of pigment dispersion: the pigment dispersion of the present example is obtained according to the disclosure of the Chinese Patent ZL 200810240447.0 (title: Pigment Dispersion, Pigment Photoresist, and Colored Filter Film, published on Dec. 29, 2010);

14.65 fractions of pentaerythritol tetraacrylate, 3.5 fractions of the aforesaid polyether compound;

4.64 fractions of the photoinitiator 2-chlorothioxanthone;

32.225 fractions of the ethyl 3-ethoxy-3-iminopropionate and cyclohexanone (volume ratio: 11:2);

0.05 fraction of the silane coupling agent A-151, 0.23 fraction of the leveling agent BYK-306, 0.02 fraction of the anti-foam BYK-065, and 0.075 fraction of the light stablizer Chisorb 292.

The aforesaid components are mixed and thoroughly agitated to provide the photoresist composition 3.

Example 4

(1) Preparation of the Polyether Compound Monomer

In the aforesaid Formula (I), $R_1$ is the polyether backbone of the polyether triol; $R_2$ is methyl; and n is 3.

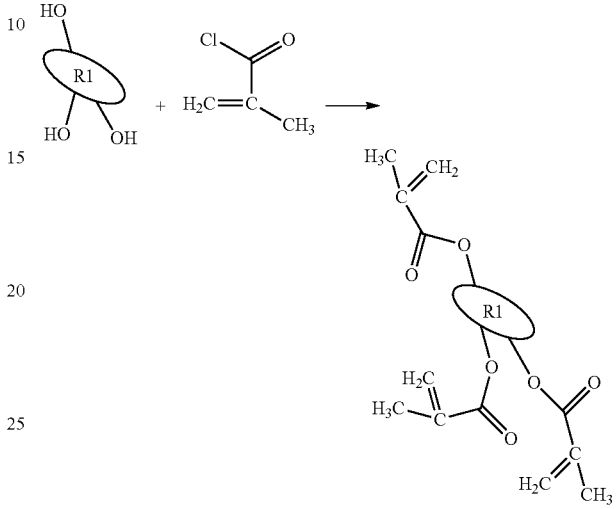

1 fraction of polyether triol (molecular weight: 4980), 0.13 fraction of the catalyst triethylamine, and 120 ml tetrahydrofuran solvent are added to the three-necked bottle by mole, and 3.5 fractions of 2-methacryloyl chloride are slowly added by dripping under ice bath. After completion of the dripping, the ice bath is removed, followed by heating to reflux under nitrogen atmosphere for 14 hours. After the completion of the reaction, 25 ml water is added under ice bath to quench the reaction, followed by filtration to remove salts and vacuum evaporation to remove tetrahydrofuran. 50 ml water is added, followed by extraction with ethyl acetate (3×100 ml). The organic layer (product) is dried with anhydrous sodium sulfate, and the solvent is spun dry under vacuum to provide the product.

The molecular weight of the product is detected by gel filtration spectrum to be 5184.

(2) Preparation of the Photoresist Composition

The components are as follows (by weight fraction):

5.0 fractions of aromatic acid methacrylate resin: the aromatic acid methacrylate resin with the product name Sarbox® SB400 is employed in the present example;

30.0 fractions of pigment dispersion: the pigment dispersion of the present example is obtained according to the disclosure of the Chinese Patent CN102977359A (application number: CN201210468331.9, title: Fluorine Containing Polymer, Method for Preparing Same, and Use thereof, Pigment Dispersion and Method for Preparing Same, published on Mar. 20, 2013);

13.25 fractions of trihydroxymethylpropane triacrylate, 2.37 fractions of the aforesaid polyether compound;

1 fraction of the photoinitiator benzoin butyl ether;

15.0 fractions of propylene glycol diacetate and 2-heptane solvent (volume ratio: 6:1);

0.021 fraction of the silane coupling agent A-186, 0.15 fraction of the leveling agent BYK-354, 0.021 fraction of the anti-foam BYK-141, and 0.015 fraction of the light stablizer Chisorb 292.

The aforesaid components are mixed and thoroughly agitated to provide the photoresist composition 4.

Example 5

(1) Preparation of the Polyether Compound Monomer

In the aforesaid Formula (I), $R_1$ is the polyether backbone of the polyether tetrol; $R_2$ is ethyl; and n is 4.

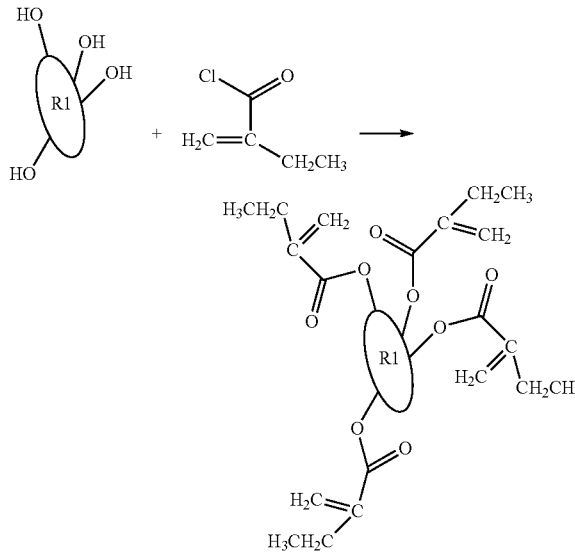

1 fraction of polyether tetrol (molecular weight: 1960), 0.12 fraction of the catalyst triethylamine, and 180 ml tetrahydrofuran solvent are added to the three-necked bottle by mole, and 4.3 fractions of 2-ethylacryloyl chloride are slowly added by dripping under ice bath. After completion of the dripping, the ice bath is removed, followed by heating to reflux under nitrogen atmosphere for 23 hours. After the completion of the reaction, 35 ml water is added under ice bath to quench the reaction, followed by filtration to remove salts and vacuum evaporation to remove tetrahydrofuran. 70 ml water is added, followed by extraction with ethyl acetate (3×140 ml). The organic layer (product) is dried with anhydrous sodium sulfate, and the solvent is spun dry under vacuum to provide the product.

The molecular weight of the product is detected by gel filtration spectrum to be 2288.

(2) Preparation of the Photoresist Composition

The components are as follows (by weight fraction):

25.0 fractions of urethane acrylate resin: the urethane acrylate resin with the model name DH-317 of Shenzhen Dinghao Actinic Tech Co. Ltd. is employed in the present example.

50.0 fractions of pigment dispersion: the pigment dispersion of the present example is obtained according to the disclosure of the Chinese Patent ZL 200810240447.0 (title: Pigment Dispersion, Pigment Photoresist, and Colored Filter Film, published on Dec. 29, 2010);

19.4 fractions of pentaerythritol tetraacrylate,
5.6 fractions of the aforesaid polyether compound;
9.22 fractions of the photoinitiator 2-chlorothioxanthone;
40.0 fractions of propylene glycol monomethyl ether acetate and ethyl 3-ethoxy-3-iminopropionate (volume ratio: 13:4);

0.02 fraction of the silane coupling agent A-151, 0.31 fraction of the leveling agent BYK-306, 0.02 fraction of the anti-foam BYK-065, and 0.095 fraction of the light stablizer Chisorb 292.

The aforesaid components are mixed and thoroughly agitated to provide the photoresist composition 5.

Example 6

(1) Preparation of the Polyether Compound Monomer

In the aforesaid Formula (I), $R_1$ is the polyether backbone of the polyether pentol; $R_2$ is hydrogen; and n is 5.

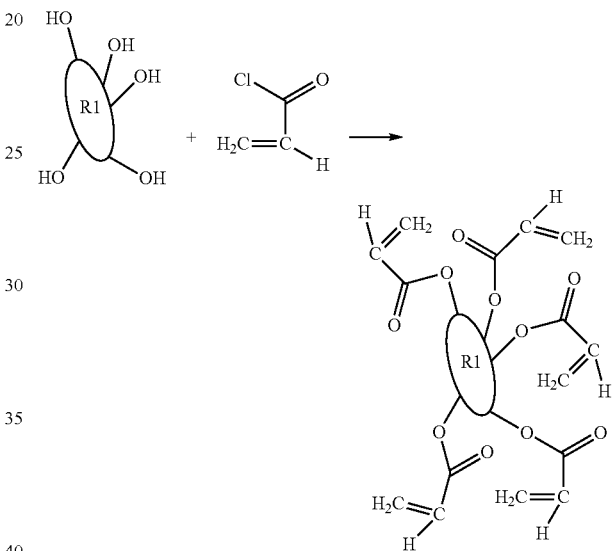

1 fraction of polyether pentol (molecular weight: 3360), 0.14 fraction of the catalyst triethylamine, and 220 ml tetrahydrofuran solvent are added to the three-necked bottle by mole, and 5.4 fractions of acryloyl chloride are slowly added by dripping under ice bath. After completion of the dripping, the ice bath is removed, followed by heating to reflux under nitrogen atmosphere for 27 hours. After the completion of the reaction, 40 ml water is added under ice bath to quench the reaction, followed by filtration to remove salts and vacuum evaporation to remove tetrahydrofuran. 90 ml water is added, followed by extraction with ethyl acetate (3×100 ml). The organic layer (product) is dried with anhydrous sodium sulfate, and the solvent is spun dry under vacuum to provide the product.

The molecular weight of the product is detected by gel filtration spectrum to be 3630.

(2) Preparation of the Photoresist Composition

The components are as follows (by weight fraction):

16.65 fractions of amine modified acrylate resin: the amino modified acrylate resin with the product name Laromer® LR 8997 is employed in the present example;

38.3 fractions of pigment dispersion: the pigment dispersion of the present example is obtained according to the disclosure of the Chinese Patent ZL 200810240447.0 (title:

Pigment Dispersion, Pigment Photoresist, and Colored Filter Film, published on Dec. 29, 2010);

15.32 fractions of pentaerythritol tetraacrylate, 2.3 fractions of the aforesaid polyether compound;

7.63 fractions of the photoinitiator 2-chlorothioxanthone;

20.12 fractions of propylene glycol monomethyl ether acetate and cyclohexanone (volume ratio: 9:1);

0.02 fraction of the silane coupling agent A-151, 0.09 fraction of the leveling agent BYK-306, 0.016 fraction of the anti-foam BYK-065, and 0.085 fraction of the light stablizer Chisorb 292.

The aforesaid components are mixed and thoroughly agitated to provide the photoresist composition 6.

Example 7

(1) Preparation of the Polyether Compound Monomer

In the aforesaid Formula (I), $R_1$ is the polyether backbone of the polyether triol; $R_2$ is ethyl; and n is 3.

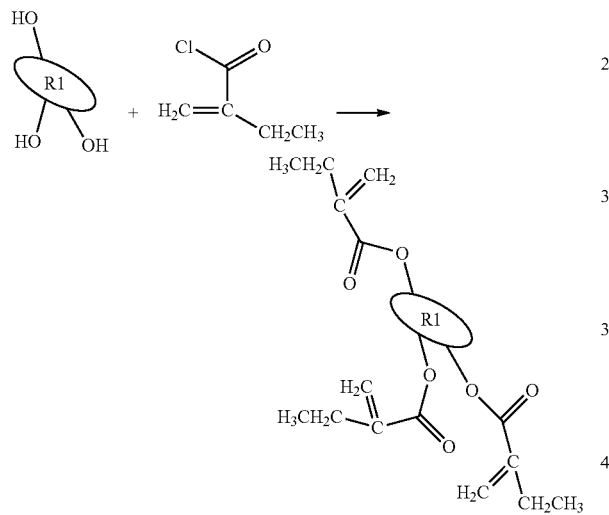

1 fraction of polyether triol (molecular weight: 5830), 0.13 fraction of the catalyst triethylamine, and 135 ml tetrahydrofuran solvent are added to the three-necked bottle by mole, and 3.5 fractions of 2-ethylacryloyl chloride are slowly added by dripping under ice bath. After completion of the dripping, the ice bath is removed, followed by heating to reflux under nitrogen atmosphere for 17 hours. After the completion of the reaction, 30 ml water is added under ice bath to quench the reaction, followed by filtration to remove salts and vacuum evaporation to remove tetrahydrofuran. 60 ml water is added, followed by extraction with ethyl acetate (3×120 ml). The organic layer (product) is dried with anhydrous sodium sulfate, and the solvent is spun dry under vacuum to provide the product.

The molecular weight of the product is detected by gel filtration spectrum to be 6076.

(2) Preparation of the Photoresist Composition

The components are as follows (by weight fraction):

18.32 fractions of urethane acrylate resin: the urethane acrylate resin with the model name DH-317 of Shenzhen Dinghao Actinic Tech Co. Ltd. is employed in the present example.

44.2 fractions of pigment dispersion: the pigment dispersion of the present example is obtained according to the disclosure of the Chinese Patent CN102977359A (application number: CN201210468331.9, title: Fluorine Containing Polymer, Method for Preparing Same, and Use thereof, Pigment Dispersion and Method for Preparing Same, published on Mar. 20, 2013);

20.25 fractions of trihydroxymethylpropane triacrylate, 3.5 fractions of the aforesaid polyether compound;

5.97 fractions of the photoinitiator 2,4-dihydrobenzophenonone;

21.68 fractions of the propylene glycol diacetate and the cyclohexanone solvent (volume ratio: 8:1);

0.023 fraction of the silane coupling agent A-186, 0.25 fraction of the leveling agent BYK-354, 0.025 fraction of the anti-foam BYK-141, and 0.02 fraction of the light stablizer Chisorb 292.

The aforesaid components are mixed and thoroughly agitated to provide the photoresist composition 7.

Example 8

(1) Preparation of the Polyether Compound Monomer

In the aforesaid Formula (I), $R_1$ is the polyether backbone of the polyether tetrol; $R_2$ is hydrogen; and n is 4.

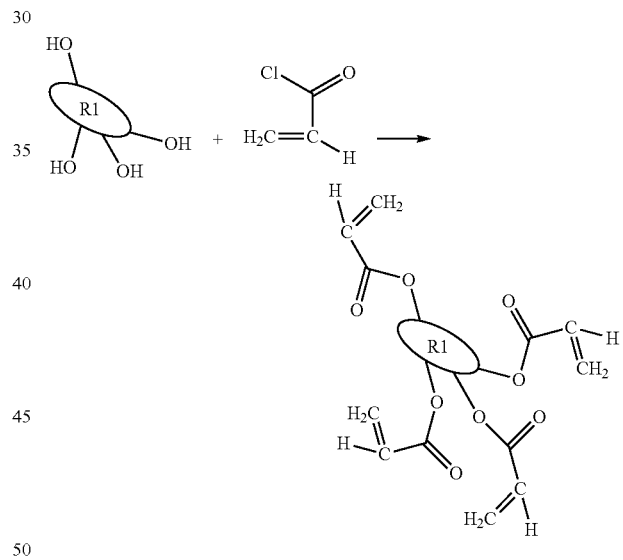

1 fraction of polyether tetrol (molecular weight: 2570), 0.14 fraction of the catalyst triethylamine, and 155 ml tetrahydrofuran solvent are added to the three-necked bottle by mole, and 4.34 fractions of acryloyl chloride are slowly added by dripping under ice bath. After completion of the dripping, the ice bath is removed, followed by heating to reflux under nitrogen atmosphere for 18 hours. After the completion of the reaction, 25 ml water is added under ice bath to quench the reaction, followed by filtration to remove salts and vacuum evaporation to remove tetrahydrofuran. 50 ml water is added, followed by extraction with ethyl acetate (3×100 ml). The organic layer (product) is dried with anhydrous sodium sulfate, and the solvent is spun dry under vacuum to provide the product.

The molecular weight of the product is detected by gel filtration spectrum to be 2786.

(2) Preparation of the Photoresist Composition

The components are as follows (by weight fraction):

20.87 fractions of amine modified acrylate resin: the amino modified acrylate resin with the product name Laromer® LR 8997 is employed in the present example;

41.2 fractions of pigment dispersion: the pigment dispersion of the present example is obtained according to the disclosure of the Chinese Patent CN102977359A (application number: CN201210468331.9, title: Fluorine Containing Polymer, Method for Preparing Same, and Use thereof, Pigment Dispersion and Method for Preparing Same, published on Mar. 20, 2013);

12.49 fractions of trihydroxymethylpropane triacrylate, 2.51 fractions of the aforesaid polyether compound;

6.3 fractions of the photoinitiator iron arene;

30.4 fractions of propylene glycol diacetate and 3-heptane solvent (volume ratio: 13:5);

0.03 fraction of the silane coupling agent A-187, 0.26 fraction of the leveling agent BYK-354, 0.017 fraction of the anti-foam BYK-141, and 0.025 fraction of the light stablizer Chisorb 292.

The aforesaid components are mixed and thoroughly agitated to provide the photoresist composition 8.

Example 9

(1) Preparation of the Polyether Compound Monomer

In the aforesaid Formula (I), $R_1$ is the polyether backbone of the polyether pentol; $R_2$ is methyl; and n is 5.

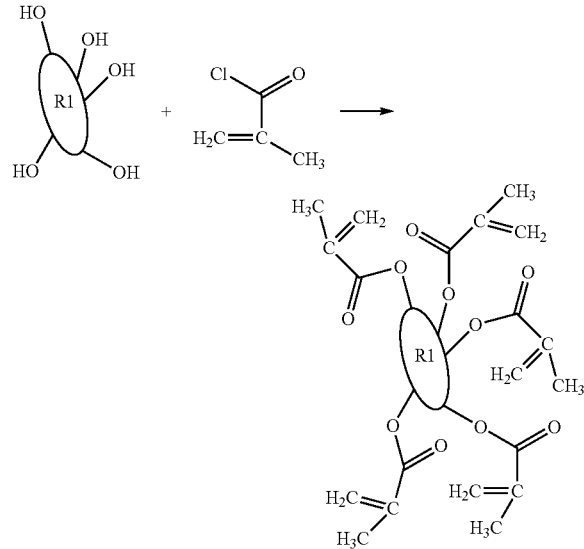

1 fraction of polyether pentol (molecular weight: 4580), 0.16 fraction of the catalyst triethylamine, and 220 ml tetrahydrofuran solvent are added to the three-necked bottle by mole, and 5.3 fractions of 2-methacryloyl chloride are slowly added by dripping under ice bath. After completion of the dripping, the ice bath is removed, followed by heating to reflux under nitrogen atmosphere for 26 hours. After the completion of the reaction, 40 ml water is added under ice bath to quench the reaction, followed by filtration to remove salts and vacuum evaporation to remove tetrahydrofuran. 90 ml water is added, followed by extraction with ethyl acetate (3×180 ml). The organic layer (product) is dried with anhydrous sodium sulfate, and the solvent is spun dry under vacuum to provide the product.

The molecular weight of the product is detected by gel filtration spectrum to be 4920.

(2) Preparation of the Photoresist Composition

The components are as follows (by weight fraction):

13.28 fractions of aromatic acid methacrylate resin: the aromatic acid methacrylate resin with the product name Sarbox® SB400 is employed in the present example;

35.5 fractions of pigment dispersion: the pigment dispersion of the present example is obtained according to the disclosure of the Chinese Patent ZL 200810240447.0 (title: Pigment Dispersion, Pigment Photoresist, and Colored Filter Film, published on Dec. 29, 2010);

17.8 fractions of pentaerythritol tetraacrylate, 3.2 fractions of the aforesaid polyether compound;

8.62 fractions of the photo initiator 2-chlorothioxanthone;

18.3 fractions of the ethyl propylene glycol monomethyl ether acetate and cyclohexanone (volume ratio: 15:1);

0.028 fraction of the silane coupling agent A-151, 0.19 fraction of the leveling agent BYK-306, 0.013 fraction of the anti-foam BYK-065, and 0.055 fraction of the light stablizer Chisorb 292.

The aforesaid components are mixed and thoroughly agitated to provide the photoresist composition 9.

Comparative Example

Except that the polyether compound monomer is replaced with equal amount of dipentaerythritol pentaacrylate, all other components and process of preparation are the same as in Example 1. The photoresist composition 10 is obtained, that is, the photoresist composition 10 having the following components (by weight fraction):

12 fractions of amine modified acrylate resin: the amino modified acrylate resin with the product name Laromer® LR 8997 is employed in the present example;

43 fractions of pigment dispersion: the pigment dispersion of the present example is obtained according to the disclosure of the Chinese Patent CN101659813B (title: Pigment Dispersion, Pigment Photoresist, and Method for Preparing Same, published on Mar. 3, 2010);

24.4 fractions of dipentaerythritol pentaacrylate;

3.5 fractions of the photoinitiator 2,4-dihydrobenzophenonone;

17.005 fractions of propylene glycol monomethyl ether acetate;

0.01 fraction of the silane coupling agent KBM0-303, 0.04 fraction of the leveling agent BYK-380, 0.02 fraction of the anti-foam BYK-057, and 0.025 fraction of the light stablizer Chisorb 292.

The aforesaid components are mixed and thoroughly agitated to provide the photoresist composition 10.

Below, the slope angles of the edges of the film layers formed from the aforesaid photoresist compositions are investigated.

The photoresist compositions prepared from Examples 1-9 as well as the comparative example are each coated onto 10 identical glass underlying substrate wherein the film layers all had thickness of 2.0 microns. They are baked in a 100° C. for 2 minutes. After radiated with 125 mJ/cm² of ultraviolet light in an exposure machine, they are developed in a development solution at the room temperature for 25-40 seconds, cleaned with deionized water, blow dried, and the film layers are cured in a 230° C. baker for 30 min.

The glass underlying substrates with the film layers prepared above are sectioned, and made into samples, which are tested using scanning electron microscopy for the sections to observe the slope angles.

Figure 2:
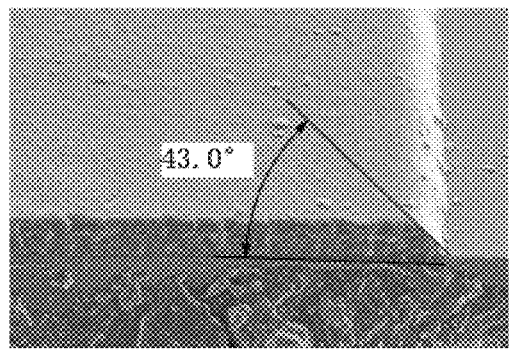
FIG. 2 is a scanning electron microscopy image of the cross section of the edge of the film layer after the photoresist composition obtained in Example 2 is made into the film.
Figure 3:
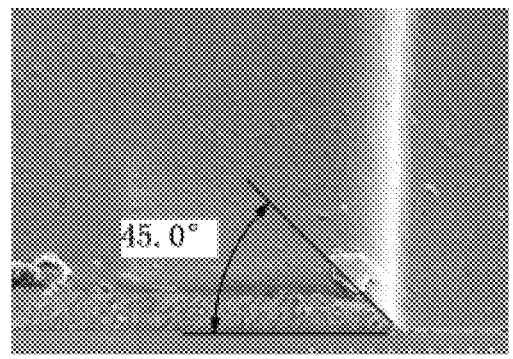
FIG. 3 is a scanning electron microscopy image of the cross section of the edge of the film layer after the photoresist composition obtained in Example 3 is made into the film.
Figure 4:
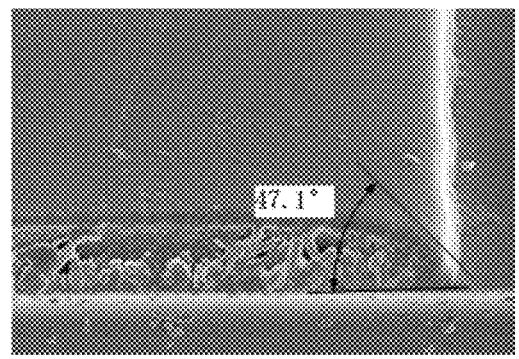
FIG. 4 is a scanning electron microscopy image of the cross section of the edge of the film layer after the photoresist composition obtained in Example 4 is made into the film.
Figure 5:
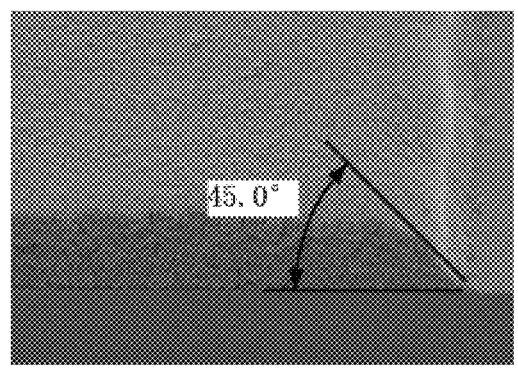
FIG. 5 is a scanning electron microscopy image of the cross section of the edge of the film layer after the photoresist composition obtained in Example 5 is made into the film.
Figure 6:
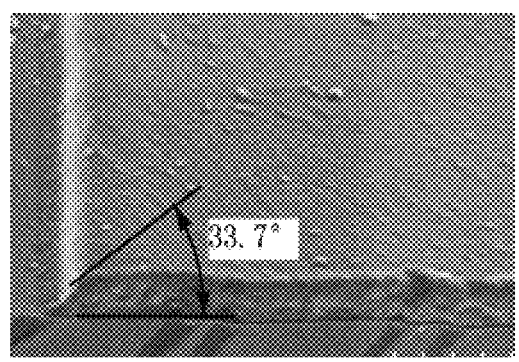
FIG. 6 is a scanning electron microscopy image of the cross section of the edge of the film layer after the photoresist composition obtained in Example 6 is made into the film.
Figure 7:
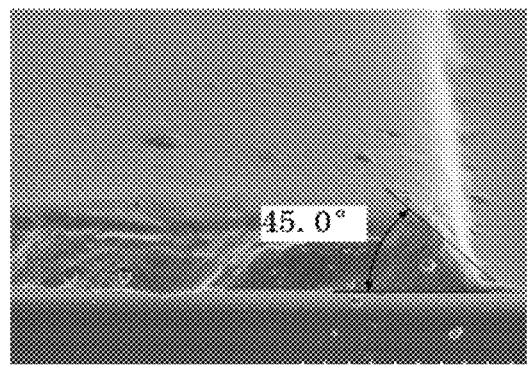
FIG. 7 is a scanning electron microscopy image of the cross section of the edge of the film layer after the photoresist composition obtained in Example 7 is made into the film.
Figure 8:
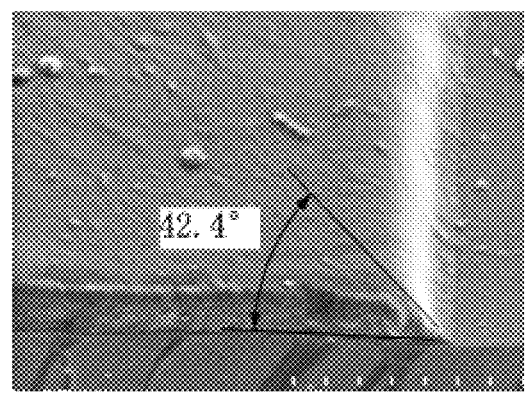
FIG. 8 is a scanning electron microscopy image of the cross section of the edge of the film layer after the photoresist composition obtained in Example 8 is made into the film.
Figure 9:
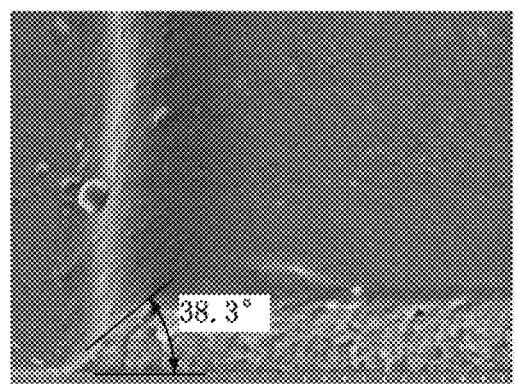
FIG. 9 is a scanning electron microscopy image of the cross section of the edge of the film layer after the photoresist composition obtained in Example 9 is made into the film.
Figure 10:
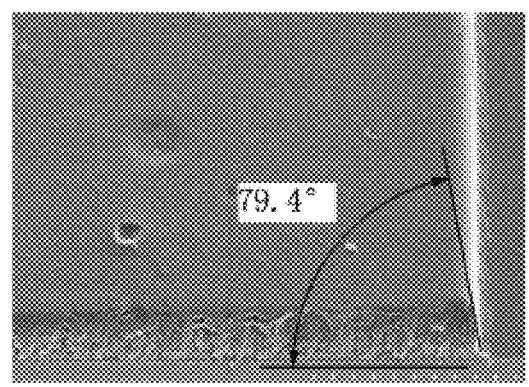
FIG. 10 is a scanning electron microscopy image of the cross section of the edge of the film layer after the photoresist composition obtained in Comparative Example is made into the film.

The figures obtained using scanning electron microscopy are shown as in FIGS. 1-10. From the figures it can be seen that the edges of the film layers obtained from the photoresist compositions 1-9 have apparently smooth slope angles, which are 53.2°, 43.0°, 45.0°, 47.1°, 45.0°, 33.7°, 45.0°, 42.4° and 38.3°, respectively, which are relatively small. In contrast, the slope of the edge of the film layer obtained from the photoresist composition 10 of the comparative example is steep, and the slope angle is large, about 79.4°.

As can be seen, after adding the polyether compound of the invention as the polymerizable monomer, the polymer thus obtained has good flexibility, and readily flows along the edge of the film layer under gravity during the high temperature post baking, making the caving of the polymer while flowing result in a smooth slope, so that the slope angle of the edge of the film layer thus formed is small. Likewise, with the lengthening of the alkyl chain, the flexibility of the polymer increases. Where the $R_2$ of the monomer for the polyether compound is a $C_3$~$C_5$ alkyl chain, it has good flexibility and when it is used for photoresist, it will make the slope angle of the film layer smaller.

The aforesaid is merely illustrative examples of the invention, rather than limits the scope of the invention. The scope of the invention is determined by the appended claims.

The invention claimed is:

1. A photoresist composition comprising a polymerizable monomer which comprises a polyether compound which is as shown in Formula (I),

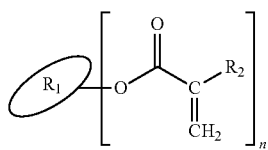

(I)

wherein $R_1$ is a polyether backbone of the polyether polyol; $R_2$ is $C_3$~$C_5$ alkyl; n is 3, 4 or 5, wherein the polymerizable monomer comprises 10%~25% by weight of polyether compound.

2. The photoresist composition according to claim 1, wherein the photoresist composition comprises by weight the following raw materials:

polymerizable monomer: 15~25 fractions;

alkaline soluble resin: 5~25 fractions;

pigment dispersion: 30~50 fractions;

photoinitiator: 1~10 fractions; and solvent: 15~40 fractions.

3. The photoresist composition according to claim 1, wherein the photoresist composition further comprises 0.0095~0.445 fraction of adjuvant.

4. The photoresist composition according to claim 3, wherein the adjuvant is one or more of a leveling agent, an anti-foam, a surfactant, a slipping agent, a silane coupling agent, or a light stablizer.

5. The photoresist composition according to claim 2, wherein the polymerizable monomer further comprises one or more of dipentaerythritol pentaacrylate, trihydroxymethylpropane triacrylate, pentaerythritol tetraacrylate or aromatic urethane acrylate.

6. The photoresist composition according to claim 2, wherein the alkaline soluble resin is alkaline soluble acrylate resin.

7. The photoresist composition according to claim 2, wherein the photoinitiator is one or more of acyl phosphosphine oxide, ketone oxime ester, benzophenone, benzoin, anthraquinone, aryl ketone or iron arene photoinitiator.

8. The photoresist composition according to claim 2, wherein the solvent is one or more of propylene glycol monomethyl ether acetate, propylene glycol diacetate, ethyl 3-ethoxy-3-iminopropionate, 2-heptane, 3-heptane, cyclopentanone or cyclohexanone.

* * * * *